United States Patent [19]

Sharkey et al.

[11] Patent Number: 5,540,701

[45] Date of Patent: Jul. 30, 1996

[54] PASSIVE FIXATION ANASTOMOSIS METHOD AND DEVICE

[75] Inventors: Hugh R. Sharkey, Redwood Shores, Calif.; Benad Goldwasser, 44 Tagor Street, Apt. 41, Tel Aviv 69341; Nachum Erlich, 63 Mendes Street, Ramat Gan, both of Israel

[73] Assignees: Hugh Sharkey, Redwood Shores, Calif.; Benad Goldwasser, Tel Aviv; Nachum Erlich, Ramat Gan, both of Israel

[21] Appl. No.: 246,984

[22] Filed: May 20, 1994

[51] Int. Cl.⁶ ............................... A61F 2/04
[52] U.S. Cl. .................. 606/153; 606/198; 623/1; 623/12
[58] Field of Search ............... 606/152, 153, 606/108, 195, 198, 200; 623/1, 12

[56] References Cited

U.S. PATENT DOCUMENTS

| | | |
|---|---|---|
| 2,897,820 | 8/1959 | Tauber . |
| 3,657,744 | 4/1972 | Ersek ........................... 606/153 |
| 4,553,543 | 11/1985 | Amarasinghe . |
| 4,784,139 | 11/1988 | Demos . |
| 4,873,977 | 10/1989 | Avant et al. . |
| 4,911,164 | 3/1990 | Roth . |
| 5,047,039 | 9/1991 | Avant et al. . |
| 5,059,211 | 10/1991 | Stack et al. ........................ 623/1 |
| 5,104,404 | 4/1992 | Wolff ................................. 623/1 |
| 5,135,536 | 8/1992 | Hillstead ........................... 623/1 |
| 5,195,984 | 3/1993 | Schatz .............................. 623/1 |
| 5,207,695 | 5/1993 | Trout, III .......................... 606/153 |
| 5,209,725 | 5/1993 | Roth . |
| 5,383,892 | 1/1995 | Cardon et al. .................... 623/12 |

FOREIGN PATENT DOCUMENTS

| | | | |
|---|---|---|---|
| 0479557 | 4/1992 | European Pat. Off. ................ 623/1 |

Primary Examiner—Gary Jackson
Assistant Examiner—William Lewis
Attorney, Agent, or Firm—Haynes & Davis

[57] ABSTRACT

A passive fixation device, defined by a generally elongated body with proximal and distal ends, and a connecting member to connect the two, is used for the anastomosis of body lumens without sutures. The proximal and distal ends are non-deployed in a non-deployed position, and are deployed in a deployed position. While in the non-deployed positions, the passive fixation device is inserted into one or more body lumens. After insertion, both the proximal and distal ends are deployed and become expanded. One end is first deployed, and then the other. The deployed proximal end becomes retained in a first lumen, and the deployed distal end becomes retained in a second lumen. In one embodiment, the first lumen is the urethra, and the second lumen is the bladder. The two lumens are permitted to become anastomized without sutures. The passive fixation device may be made of different materials and can have coiled proximal and distal ends that are expanded to their deployed positions by a Foley catheter. Additionally, the passive fixation device can be a tightly wound coil that is self-deployed when it is advanced out of a delivery catheter. The coil can also be made of a shaped memory metal. At certain temperatures, it becomes deployed. With a change in temperature, either higher or lower, the coil collapses, and is then removed from the respective body lumen.

11 Claims, 6 Drawing Sheets

PASSIVE FIXATION ANASTOMOSIS METHOD AND DEVICE

BACKGROUND OF THE INVENTION

1. Field of the Invention

This invention relates to a method and apparatus for joining together two or more hollow body lumens, and more particularly, to a method and apparatus for anastomosis of body lumens without the use of sutures, staples or clamps.

2. Description of Related Art

There are many surgical procedures requiring the connection of vessels, hollow organs and other structures, collectively body lumens. Coronary surgery is an example of such a procedure. In certain heart operations where bypass surgery is performed, sections of a coronary artery to the heart may either by completely replaced, or actually bypassed during heart bypass surgery. While some of these arteries are large, and more easily manipulated by the surgeon, other body lumens are smaller and more difficult to manipulate and hold in position while joining ends thereof after a transectional operation. These procedures typically use devices that employ staples, clamps or sutures.

More specifically to surgical procedures involving the prostate, radical retropubic prostatectomy is an established method for the treatment of patients with localized carcinoma of the prostate gland. Additionally, a prostatectomy may be performed for a variety of different medical reasons. Complications include intraoperative hemorrhage, postoperative erectlie impotence, stricture formation as well as possible disruption of the urogenital diaphragm which can render the patient incontinent. Unfortunately, impotence and incontinence are frequent occurrences resulting from many known radical prostatectomy procedures.

Prostatectomy usually involves division of the urethra at the apex of the prostate and removal of the prostate, and the stump of the urethra can retract into the adjacent tissue, the urogenital diaphragm. Two significant challenges to the surgeon are reexposure of the urethra, as well as avoiding nicking the urogenital diaphragm while performing an anastomosis of the urethra to the bladder.

Essentially, the procedures performed to date require that the surgeon grasp the end of the transected urethra and stretched it to the mating end of the urethra at the bladder with one hand, and with the other hand perform delicate suturing with tiny, fine needles. Microsurgery of this nature is highly dependent on the skill of the surgeon. Some are much better at this kind of delicate surgery than others.

A number of different microsurgery solutions, many of which are suitable to a variety of surgical procedures, have been proposed. In U.S. Pat. No. 4,553,543, a plurality of flexible suture needles are held in place in slots in a flared core by a sleeve that extends about the flexible suture needles and the core. The suture needles, and attached threads, penetrate the walls of a body duct, such as a blood vessel, by inserting the flared end of the core into the severed body duct. Needles are then forced to move longitudinally in the slots against the flared end of the core so that they bend outwardly, and are driven through the wall of the duct.

A number of patents have issued relating to anastomosis and tissue ligation, including: U.S. Pat. Nos. 2,897,820; 4,784,139; 4,911,164; and 5,209,725. Patents that directed to urethra and bladder anastomosis include: U.S. Pat. Nos. 4,848,367; 4,873,977; and 5,047,039.

The patents for urethra and bladder anastomosis involve suturing or other non-passive fixation techniques. As previously mentioned, if the urogenital diaphragm is nicked, as can occur with sutures, then the patient may become incontinent. Accordingly, it would be desirable to provide a passive fixation device and method which does not require sutures or other types of invasive treatment. Such an apparatus and method would be useful in a variety of surgical procedures where it is necessary to join two body lumens.

SUMMARY OF THE INVENTION

Accordingly, it is an object of the present invention to provide a passive fixation method and apparatus for general use in the anastomosis of body ducts, vessels, organs, and other structures, collectively body lumens, without the use of sutures, staples or clamps.

Another object of the present invention is to provide a passive fixation method and apparatus for anastomosis of the urethra to the bladder without the use of sutures, staples or clamps.

Still a further object of the present invention is to provide a method and apparatus for anastomosis of body lumens without sutures, staples or clamps, that is removable from the body once anastomosis is complete.

Another object of the present invention is to provide a method and apparatus for anastomosis of body lumens that dissolves or is absorbed by the body once anastomosis is complete.

Yet another object of the present invention is to provide an anastomosis device that includes a passive fixation device and a catheter that activates the passive fixation device once it is inside the desired lumen, with the catheter being removed after the passive fixation device has become retained in the lumen.

These and other objects of the present invention are achieved with a passive fixation device defined by a generally elongated body with a proximal end and a distal end. The ends are connected by a connecting member. Both ends are non-deployed in a non-deployed position, and are deployed in a deployed position. While in the non-deployed positions, the passive fixation device is inserted into one or more body lumens. After insertion, both the proximal and distal ends are deployed and become expanded. One end is first deployed, and then the other. The deployed proximal end becomes retained in a first lumen, and the deployed distal end becomes retained in a second lumen.

In one embodiment, the first lumen is the bladder, and the second lumen is the urethra. The passive fixation device is positioned around a Foley type catheter that includes two inflatable balloons. The catheter, with the passive fixation device, is inserted into the urethra. The first balloon is inflated, causing the proximal end of the passive fixation device to become expanded to its deployed position and become retained in the urethra. At this time, the distal end of the catheter is either in the bladder, or if not then it is moved towards the bladder. Because the expanded deployed proximal end is now retained in the urethra, the urethra is also moved towards the bladder. The catheter passes through the urogenital diaphragm without causing any nicks or disruptions to its structure. After the proximal end of the passive fixation device has been introduced into the bladder in its non-deployed position, it becomes deployed, expanded and retained in the bladder. The urethra and bladder are now positioned in a contact or almost contact relationship so that the two can become anastomized. After each end of the passive fixation device is deployed, the associated balloon of the catheter is deflated. Once the proximal end of the passive fixation device is positioned and retained in the bladder, the catheter is then removed. Because the connecting member is of a much smaller size than either of the proximal or distal ends, typically only a single strand of wire or small sheet or material, its interaction with the urogenital diaphragm is very limited. The risk of incontinence is minimized.

The passive fixation device can have coiled proximal and distal ends that are connected with a single strand of wire. Alternatively, it can be made of one or more sheets of material that can be expanded to the deployed positions. Preferably, the sheets include a plurality of perforations so that after anastomosis is complete the sheets can be gently unraveled along the perforations for easy removal through the urethra. When the coil is used, it becomes uncoiled after anastomosis and is also easily removed through the urethra with a resectoscope. Additionally, the proximal and distal ends of the passive fixation device can have different geometric configurations, depending on the application. Each may be conical, cylindrical as well as other geometries that are suitable for positioning and retaining the respective end in a desired body lumen.

The passive fixation device may consist of a tightly wound coil that becomes self-deployed as it is advanced out of a delivery catheter. Additionally, the passive fixation device can be made of a shaped memory metal. At either elevated or lower temperatures the coil is deployed, or it collapses, allowing it to be removed through itself.

A variety of different materials can be used for the passive fixation device. The coil can constitute different gauges of wire, depending on the body lumens to be anastomized. Both non-metals and metals can be used. Memory metals are suitable, as well as materials that are absorbable and dissolvable. Some dissolvable materials gradually dissolve as anastomosis proceeds, and can be passed through the urine when the application is the anastomosis of the bladder to the urethra. Other dissolvable materials can be activated with an initiating media such as ultra-sound.

Advantageously, the present invention provides a method and apparatus for the anastomosis of body lumens without the use of sutures, staples or clamps. It is particularly useful for the anastomosis of the urethra and bladder following prostatectomy because the urogenital diaphragm is not disrupted and the change of nicking it are greatly reduced. The present invention is suitable with other surgical and microsurgical applications, particularly when it is desirable to avoid suturing.

DETAILED DESCRIPTION OF THE DRAWINGS

DETAILED DESCRIPTION OF THE PREFERRED EMBODIMENTS

Figure 1:
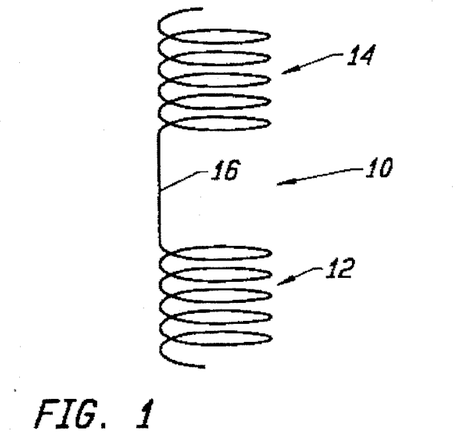
FIG. 1 is a perspective view of one embodiment of the passive fixation device with coiled proximal and distal ends that are connected with a single strand of wire. The ends are in non-deployed positions.
Figure 2:
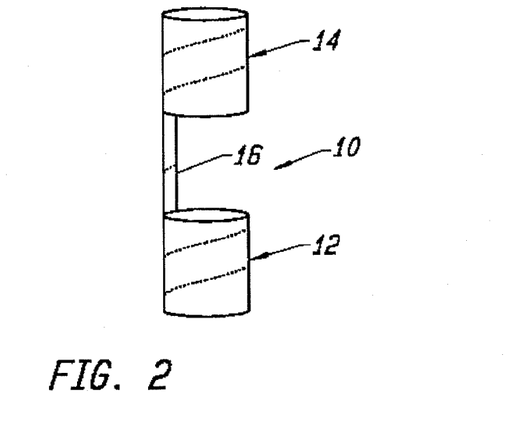
FIG. 2 is a perspective view of a second embodiment of the passive fixation device made of one or more sheets of an expandable solid material that includes a plurality of perforations formed in the solid. The ends are connected by a single piece of solid material that has a much narrow cross-sectional area than the diameter of either of the proximal or distal ends. Both ends are shown in non-deployed positions.
Figure 3:
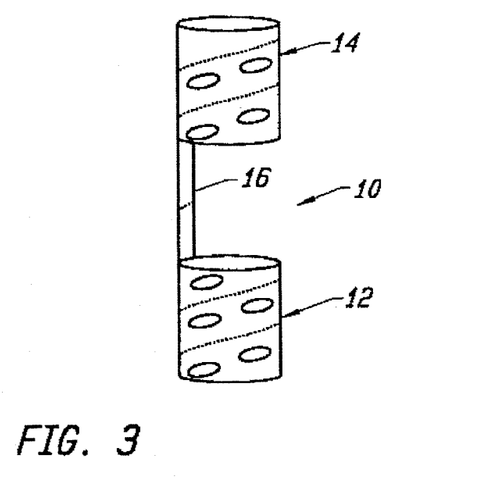
FIG. 3 illustrates a third embodiment of the passive fixation device, in the non-deployed position. The solid material includes a plurality of perforations as well as apertures, thus making it a semi-solid structure.

A passive fixation device, suitable for the anastomosis of vessels, ducts, organs, or other body structures, collectively body lumens, is illustrated in FIGS. 1 through 3. For purposes of the present invention, a passive fixation device is one where ends or areas of body lumens are brought together in an adjacent, or nearly adjacent relationship, held there a sufficient length of time in order to permit anastomosis of the lumens to occur without the use, or alternatively the minimal use of sutures, staples, clamps, or other invasive retaining structures. Preferably, anastomosis proceeds without the use of such invasive retaining materials.

A generally elongated body 10 with a proximal end 12, a distal end 14 and a connecting section 16. Ends 12 and 14 can be in deployed and non-deployed positions. In FIGS. 1 through 3, ends 12 and 14 are illustrated as being in non-deployed positions. In the non-deployed positions, passive fixation device 10 is inserted into a desired body lumen, including but not limited to the urethra and bladder. The non-deployed positions provide for the easy introduction of passive fixation device 10 into the body lumen, without damaging the lumen. If passive fixation device 10 is introduced into the body lumen in a deployed position, then it is far more difficult to insert device 10 into the lumen without cutting, shearing, tearing or imparting some other sort of damage to the lumen.

In FIG. 1, passive fixation device 10 is made of a coiled proximal end 12, coiled distal end 14 and a single strand of connecting medium, including but not limited to a wire-like structure. Coiled ends 12 and 14 are shown as being generally cylindrical in the non-deployed positions, but other geometric configurations are possible. In FIG. 2, passive fixation device 10 is made of a generally solid material, which may consist of one or more sheets. Preferably, the solid material includes a plurality of perforations in order to facilitate the removal of passive fixation device 10 from the confined area once anastomosis is complete, or nearly complete, as more fully explained hereafter in this specification. Ends 12 and 14 are connected by a generally narrow, connecting section 16, made of preferably the same material as ends 12 and 14. FIG. 3 shows that instead of a completely solid structure, passive fixation device 10 can be made of a generally solid material. In FIG. 3, one embodiment is shown where the solid material is semi-solid and includes a plurality of apertures and perforations. The solid material has sufficient structural integrity so that it can be expanded to the deployed position and remain deployed so that ends 12 and 14 become retained in their respective lumens. Thus instead of the coiled structure of FIG. 1, it is possible to employ a solid structure, or one that is nearly solid, so long as in the deployed position ends 12 and 14 remain sufficiently expanded and deployed to be retained in the desired lumen.

Figure 4:
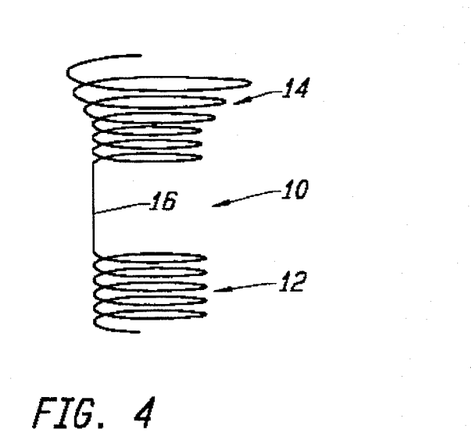
FIG. 4 shows a coiled passive fixation device in a deployed position. The proximal end is expanded to a generally cylindrical geometry, while the distal end is substantially conical.
Figure 5:
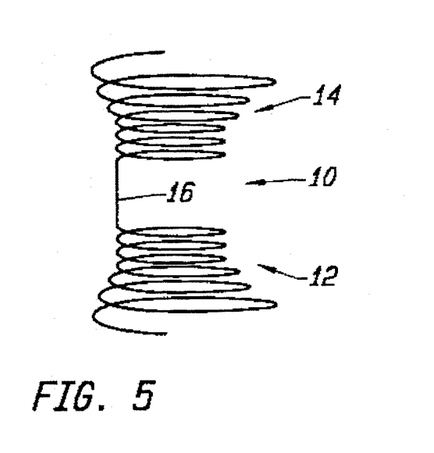
FIG. 5 shows a coiled passive fixation device in a deployed position with both the proximal and distal ends expanded to generally conical geometries.
Figure 6:
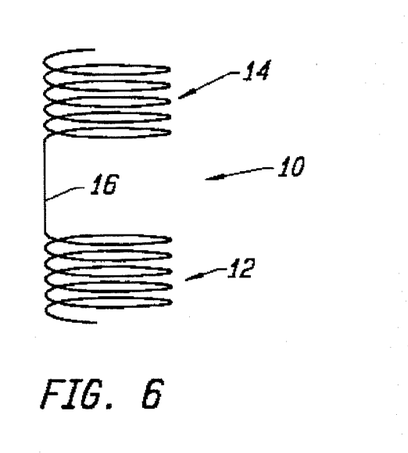
FIG. 6 illustrates a coiled passive fixation device in a deployed position with both the proximal and distal ends expanded to generally cylindrical configurations.
Figure 7:
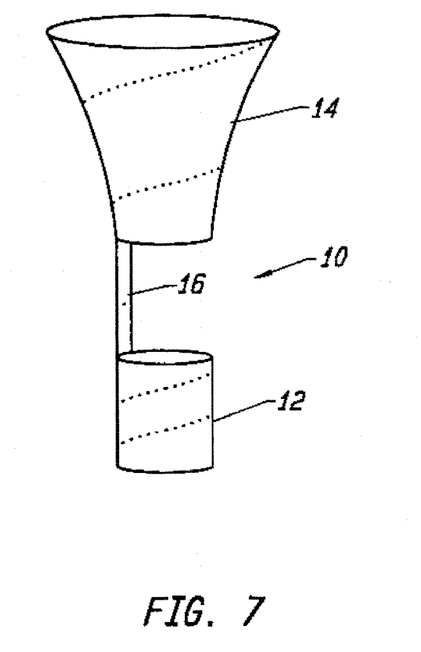
FIG. 7 illustrates the passive fixation device of FIG. 2 in a deployed position with the proximal end expanded to a cylindrical configuration, and the distal end expanded to a generally conical shape.
Figure 8:
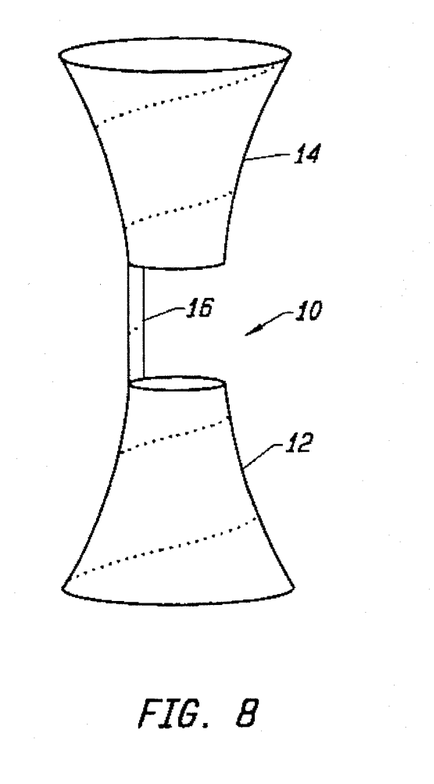
FIG. 8 illustrates the passive fixation device of FIG. 2 in a deployed position with both the proximal and distal ends expanded to generally conical configurations.

FIGS. 4 through 8 show ends 12 and 14 in different deployed geometric configurations. In FIG. 4, proximal end 12 is deployed to a generally cylindrical shape while distal end 14 is expanded to a conical configuration. Proximal and distal ends 12 and 14 are expanded to conical geometries in FIG. 5, while in FIG. 6, proximal and distal ends 12 and 14 are expanded to generally cylindrical shapes. In FIGS. 7 and 8, passive fixation device 10 is made of a substantially solid material and proximal and distal ends 12 and 14 are expanded to conical and cylindrical geometries respectively.

While proximal and distal ends 12 and 14 are inserted into desired body lumens, they are usually in the non-deployed positions in order to permit easy insertion with minimum disruption to the body lumen. In deployed positions, each end 12 and 14 is expanded so that least a portion of the end has a diameter that is greater than at least a portion of the body lumen where it is deployed. In this manner, proximal and distal ends 12 and 14 are retained within the lumens and become temporary fixed therein until anastomosis is complete, or complete enough so that passive fixation device 10 can be removed from the lumen. Sufficient expansion in the deployed position is produced in order to achieve the desired retaining effect. For example, if two vessels are to be joined, proximal and distal ends 12 and 14 are initially positioned in the two vessels in non-deployed positions. They are subsequently deployed, causing each end 12 and 14 to have at least a portion with a diameter that is greater than at least a portion of the lumen's diameter in which ends 12 or 14 become retained. If the lumen is a body organ, either proximal or distal end 12 or 14 is inserted into the organ in the non-deployed position, and then expanded to the deployed position with at least a portion of its diameter greater than at least the diameter of one section of the organ, permitting the deployed end to become "seated" in the organ.

Referring once again to FIG. 1, and without limiting the scope of the present invention, in one embodiment passive fixation device 10 has a proximal end 12 with length of about 1.5 cm, connecting member 16 length of about 2.5 cm and distal end 14 length of about 2.5 cm. The coil is made of 32 French wire.

A variety of materials can be used for passive fixation member 10, including but not limited to materials suitable for coiling such as different gauges of wire. The wire can be made of biocompatable materials including various metals such as copper, nitinol and memory wire. Additionally, a wire like structure can become coiled with the application of a first current, and uncoiled when a second is applied. Different solid materials, or semi-solid materials, that can be used include but are not limited to plastics, polyester, polyolefin, nylon, polyurethane, and the like. Other suitable materials are absorbable by the body once anastomosis is sufficiently completed that passive fixation device 10 is no longer needed. Additionally, dissolvable materials, that can pass through the body, for example with different body fluids such as blood, urine, and the like, can be used. Some of the materials can be dissolved upon the application of an activating mechanism including but not limited to ultrasound. A tab 12 can incorporated into either end of proximal or distal ends 12 and 14, in order to facilitate remove of passive fixation device 10 from the body structure. The tab can be in the form of a turned up bead that can be lifted up away from its point of contact with a body lumen, and then it is pulled out through itself. This is particularly useful when distal end 14 is unseated and the coil pulls through itself with minimal disruption of body lumens. The tab can also serve the purpose, in certain applications, of being seated within the body lumen so as to engage and retain proximal or distal ends 12 and 14 therein.

Figure 9:
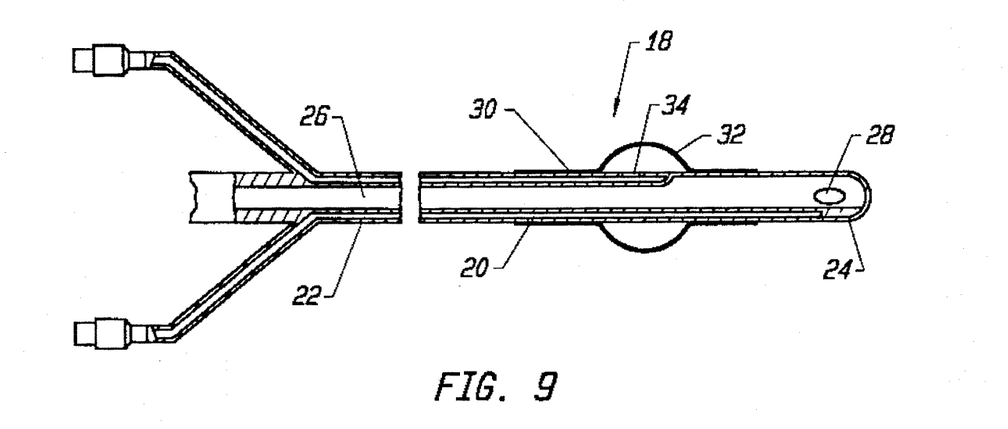
FIG. 9 is a cross-sectional view of a Foley type catheter, with expanded balloon, used in certain embodiments with the passive fixation device.

Passive fixation device 10 can be inserted into a body lumen with the use of a catheter, such as a Foley catheter 18 of FIG. 9. Foley catheter 18 is particularly useful for urology applications, but it will be appreciated that the present invention is not limited to urology. For purposes of the following discussion, the use of Foley catheter 18 will be for anastomosis of a urethra with a bladder following a prostatectomy.

Figure 12:
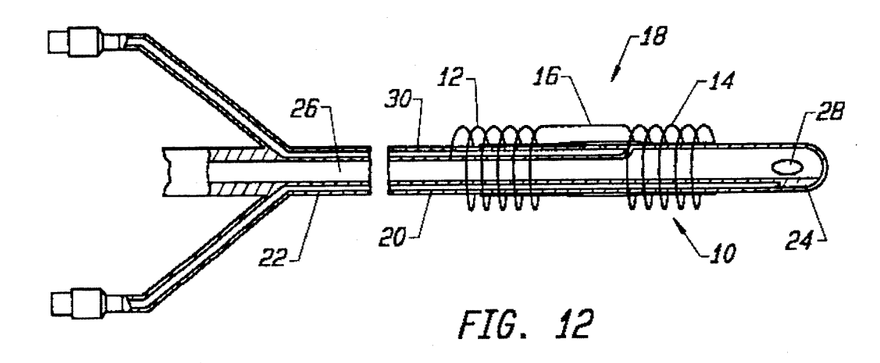
FIG. 12 illustrates the placement of the passive fixation device in an adjacent surrounding relationship to the Foley catheter of FIG. 11 in a non-deployed state.

Catheter 18 has en elongated tube 20 that has a proximal end 22 that remains outside of a patient's body, and a distal end 24 that is eventually placed in the patient's bladder. Catheter 18 is inserted through the urethra as shown in FIG. 12. Elongated tube 20 includes a main lumen 26 extending from an inlet opening 28, located at distal end 24 of catheter 18, to proximal end 22.

An inflation lumen 30 extends through elongated tube 20 connecting a source of fluid located at the exterior to the patient's urethra (not shown) at proximal end 22 to a balloon 32. Inflation lumen 30 terminates in an inflation outlet 34 formed in elongated tube 20. Introduction of fluid causes balloon 32 to inflate, and it deflates when the fluid is removed.

Figure 11:
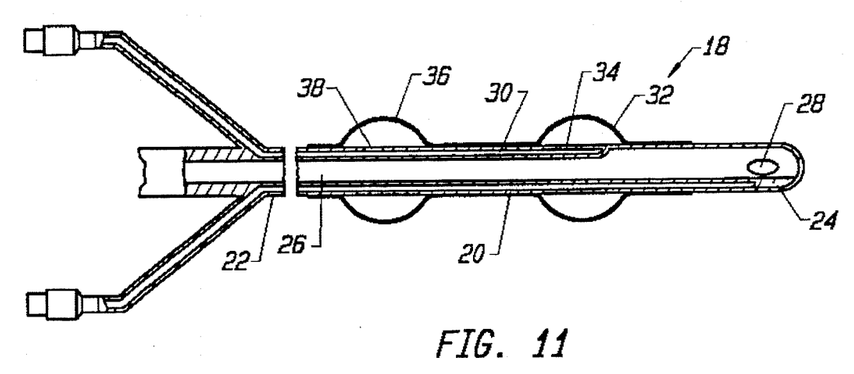
FIG. 11 is a cross-sectional view of a Foley type catheter with two expanded balloons. The first balloon has a generally spherical shape, while the second one is conical.
Figure 13:
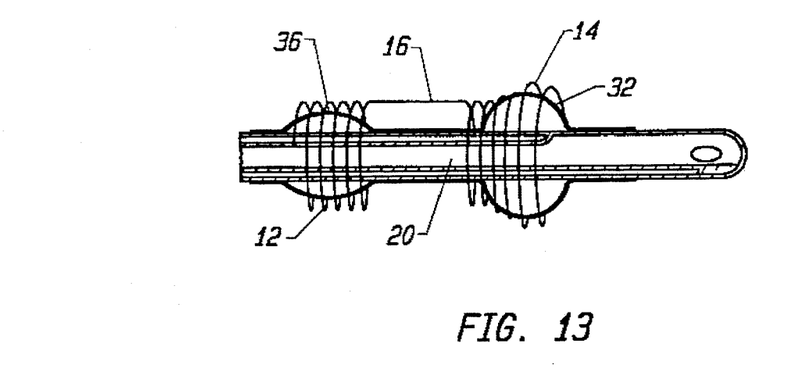
FIG. 13 illustrates the placement of the passive fixation device around the Foley catheter of FIG. 11. Both balloons have been expanded to deploy the passive fixation device. The proximal end has been expanded with a spherical balloon, and the deployed proximal end has a cylindrical geometry. The distal end has been expanded with a conical shape balloon which imparts a conical geometry to the distal end of the passive fixation device.

As shown in FIG. 11, catheter 18 includes two balloons, 34 and 36 which are inflated by one or more inflation lumens 30 and 38. This embodiment is particularly suitable for use of passive fixation device 10 following prostatectomy for the anastomosis of the urethra with the bladder in a sutureless procedure. Passive fixation device 10 is positioned around the exterior of elongated tube 20 in FIG. 12. In FIG. 13, passive fixation device 10 is positioned so that balloons 32 and 36 are inflated, causing proximal end 12 and distal end 14 to be expanded to their deployed positions.

Catheter 18 can also include one or more distensible members that are mechanically extended and retracted in order to deploy proximal and distal ends 12 and 14 of passive fixation device. An actuator causes the distensible members to become mechanical distended. After proximal and distal ends are deployed, the distended ends are retracted. The distensible members can be used in place of balloons 32 and 36.

The geometry of balloons 32 and 36 can be such that when inflated they impart various geometrical configurations that are then used to expand proximal and distal ends 12 and 14. As shown in FIG. 13, balloon 32 is inflated to a conical shape, causing distal end 14 to become expanded to the conical coil shown in FIG. 4. Balloon 36 expands spherically, causing proximal end 12 to become cylindrically expanded, as also shown in FIG. 4. Other geometries of balloons 32 and 36 are possible, depending on the desired deployed shape of distal end 14 and proximal end 12. It will be appreciated that the deployed proximal and distal ends 12 and 14 of passive fixation device 10 can be initially formed such that when an expanding force, such as imparted by either balloon 32 or 36, is applied to ends 12 and 14 they will form the desired deployed geometries. For example, a coil may be wound with various degrees of winding intensity such that with an even application of force, such as with a spherical balloon, it will become deployed in a conical geometry.

Figure 10:
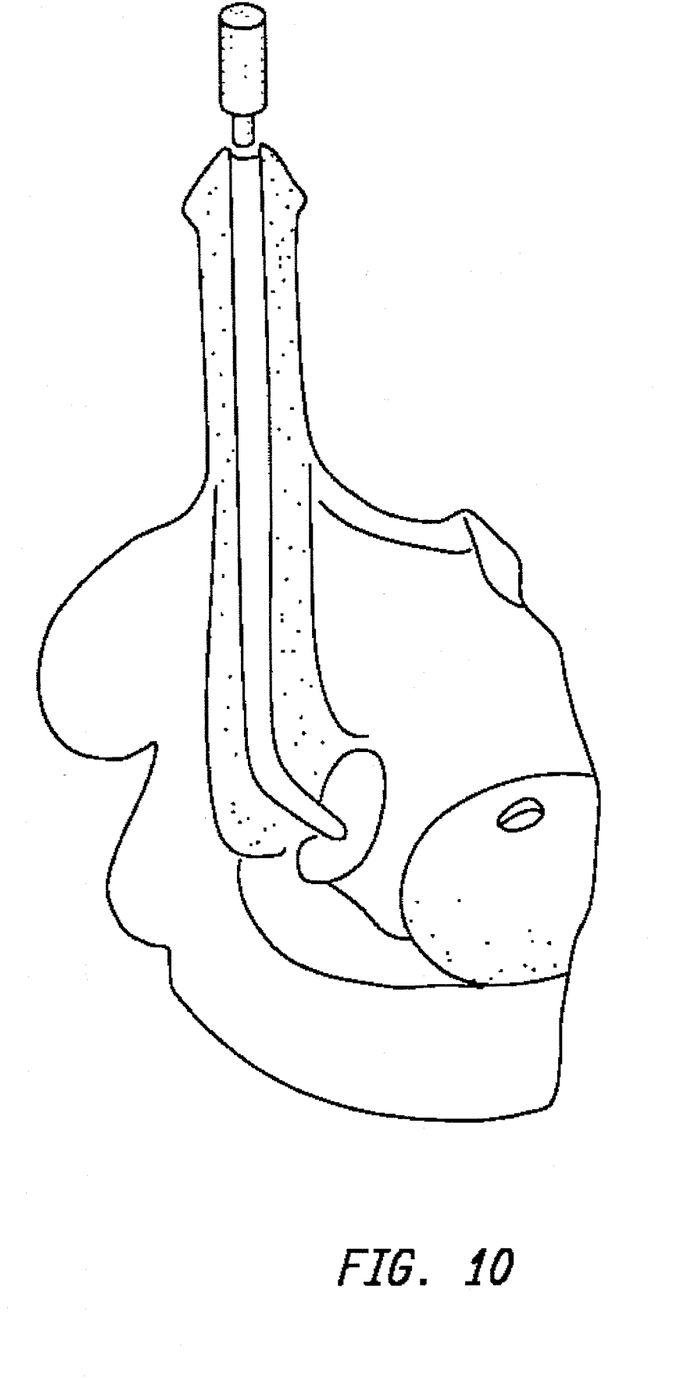
FIG. 10 illustrates the human urological anatomy, and the introduction of the Foley catheter into the urethra.
Figure 14:
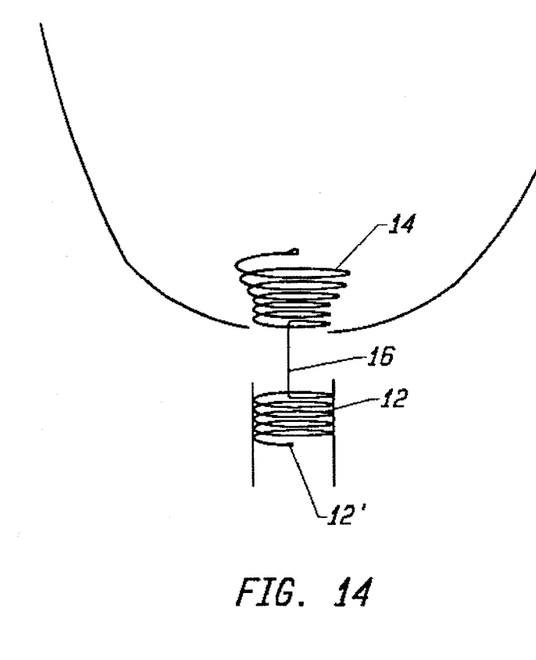
FIG. 14 shows placement of the passive fixation device in the urethra and bladder after deployment, with the proximal end of the passive fixation device being expanded to be retained in the urethra, and the distal end expanded so that is seated and retained in the bladder.
Figure 15:
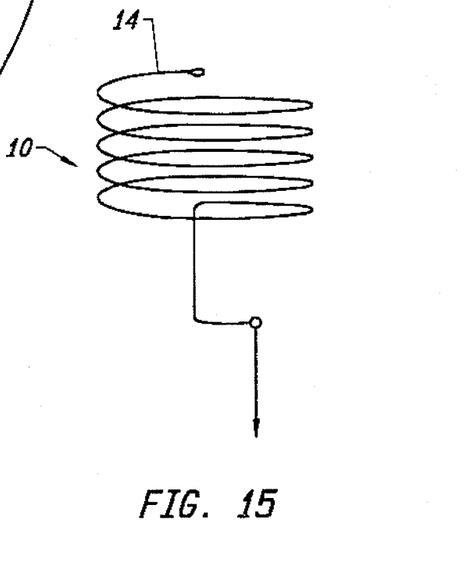
FIG. 15 illustrates one method of uncoiling and removing a coiled passive fixation device by pulling on either end of the coil.

With reference again to FIG. 12, catheter 18 and passive fixation device 10 are inserted into the urethra, as shown in FIG. 10, following the removal of the prostate. While inserted into the urethra, proximal and distal ends 12 and 14 of passive fixation device are in non-deployed positions. As proximal end 12 is near the distal end of the urethra it is deployed and expands to a cylindrical, conical or other geometric configuration, such that proximal end 12 becomes retained in the urethra. Balloon 36 can then be deflated. At this time, distal end 14 of passive fixation device 10 may already be within the bladder. If not, then catheter 18 is advanced further, without disrupting the urogenital diaphragm, with distal end 24 of catheter 18, and distal end 14 of passive fixation device, entering the bladder. Balloon 32 is then deployed, causing distal end 14 to become deployed in a conical or other suitable geometry so that distal end 14 becomes retained within the bladder. As catheter 18 is advanced into the bladder, the distal end of the urethra is moved in a position adjacent, or nearly adjacent to the bladder. As shown in FIG. 14, upon deployment of distal end 14 of passive fixation device 10, the bladder and distal end of the urethra are urged towards each other in a relationship that permits anastomosis between the two. Now that passive fixation device 10 is retained in both the urethra and bladder, catheter 18 can be removed, or it can remain for a desired time to permit drainage of urine through catheter 18.

After a time period, such as for example, but not limited to thirty (30) days, anastomosis is essentially complete. Passive fixation device 10 can then be removed. Alternatively, it may have already become absorbed by the body or dissolved and passed through the urine.

Figure 16:
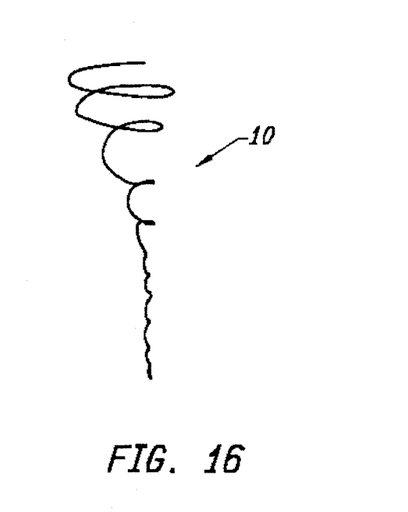
FIG. 16 illustrates the uncoiling of the coil of FIG. 15.
Figure 17:
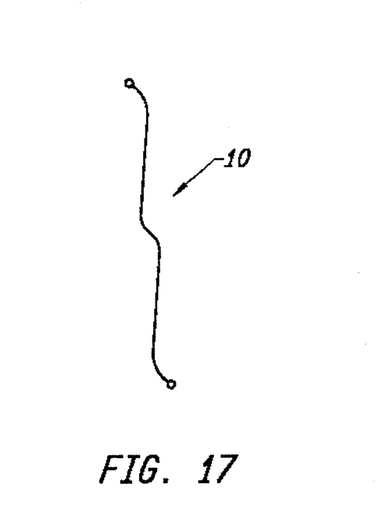
FIG. 17 shows that the coil has become substantially uncoiled as it is removed from a body structure such as the urethra.

Passive fixation device 10 is readily removed by using a resectoscope, or other suitable instrumentation, to physically grab either proximal or distal end 12 and 14 and pull. The unwinding of the coil is shown in FIG. 16. It will be appreciated that distal end 14 of passive fixation device 10 can be uncoiled when a resectoscope, cystoscope, or the like grabs distal end 14 at the turned up bead portion, unseats the bead from the interior of the body lumen, distal end is then pulled out through passive fixation device 10 and readily is uncoiled, removed through itself with minimal disruption to body lumens. FIG. 17 illustrates that the coil becomes generally elongated as it is unwound and is readily removed through the urethra. If passive fixation device 10 is made of a solid material with perforations, then the resectoscope grabs the solid material and unwinds it along the perforations as the resectoscope is pulled away from the bladder.

It will be appreciated that the present invention is applicable to a variety of body lumens other than the urethra and bladder.

Figure 18:
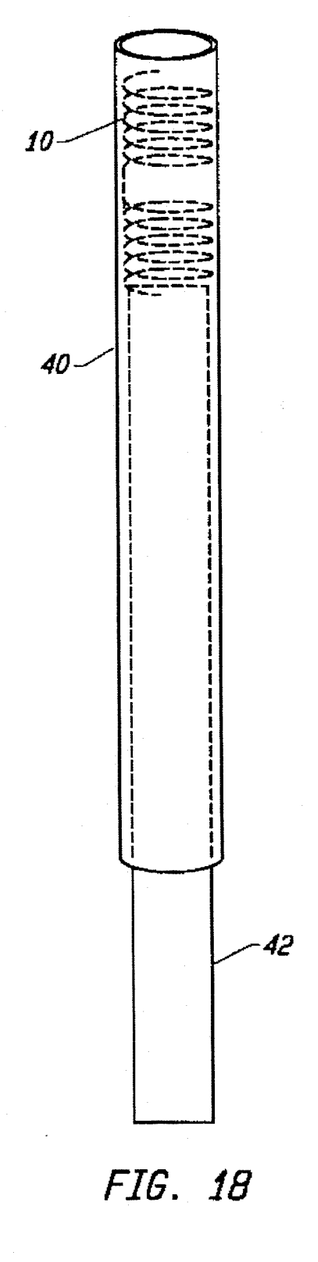
FIG. 18 illustrates a tightly wound coil positioned in a delivery catheter.
Figure 19:
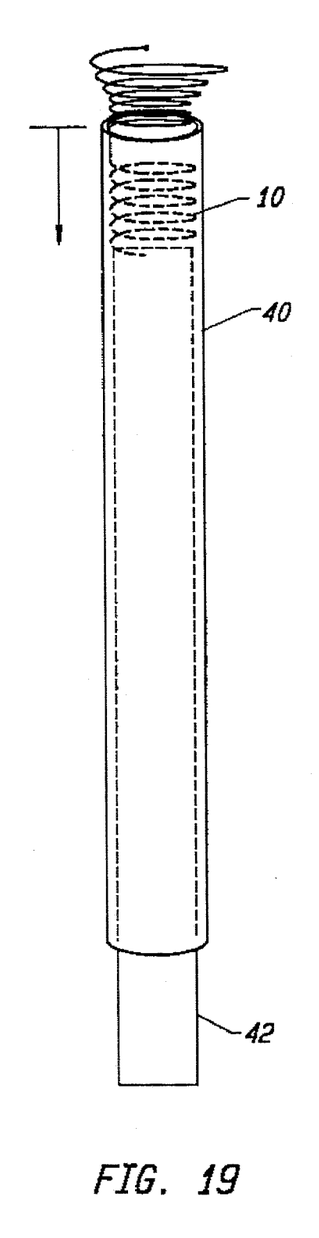
FIG. 19 illustrates a tightly would coil, positioned in a delivery catheter, with a cam advancing the coil out of the delivery catheter.
Figure 20:
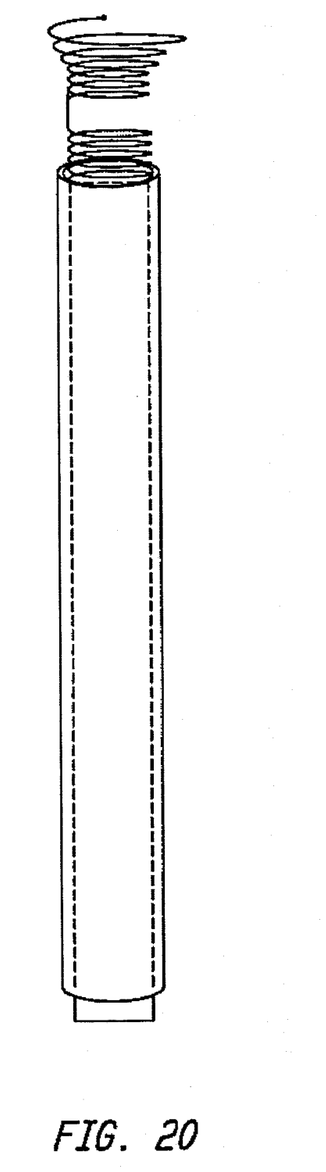
FIG. 20 illustrates the deployed coil after it has been removed from the delivery catheter.

In another embodiment of the invention, passive fixation device 10 has proximal and distal ends 12 and 14 respectively, that are tight coils in the non-deployed (deactivated) states, and each end becomes self expanded in the deployed (activated) state. In this embodiment, passive fixation device 10 is a tight coil when it is positioned and delivered through the use of a delivery catheter 40 (FIG. 18). Passive fixation device 10 can be placed in the desired body lumen, and its position can be determined by including a platinum, gold, or the like marker at distal end 14. Through the use of ultra sound, or the like, the position of distal end 14 is then determined. Passive fixation device 10 can be a coil, cone or the like, however, for ease of discussion will be referred to as a coil, is wound tightly and is in non-deployed (deactivated) state and must be contained or it will become deployed without the use of balloons or some mechanism to expand it. The coil fits easily within the lumen of delivery catheter 40. Delivery cathode 40 is then pulled away from the desired body lumen where the coil is to be positioned, and with the removal of delivery cathode 40 the coil begins to unwind to its deployed (activated) state. The unwinding of the coil, with the removal of delivery catheter 40 is illustrated in FIG. 19. Optionally, delivery catheter 40 can include a mandrel 42 which pushes the coil out of delivery catheter 40. Mandrel 42 is of sufficient size to occlude the lumen, like a ram rod, yet remain longitudinally manipulable over the tortuous course of a body lumen like the urethra or other delivery path. Delivery catheter 40 can be still, to aid in the positioning of the coil. As is shown in FIG. 20, the coil is fully deployed once delivery catheter 40 is removed. It will be appreciated that a solid sheet of material, in place of the wound coil, can also be employed with this embodiment.

As previously mentioned, the coil can be made of a shaped memory metal, such as nickel titanium, available from Raychem, Menlo Park, Calif. In one embodiment, the coil is heated and expanded. Additionally, the coil can be preloaded so at a temperature, such as 37 degrees C, it is expanded. At 20 degrees C, it remains as a tight coil and non-deployed. In this instance, the body lumen itself provides the heat to deploy the coil. It is initially at this lower temperature. When introduced into the desired body lumen, it becomes deployed with the heat from the body lumen. The coil can be cooled before insertion and activated with an electrical current. It is also possible to heat the coil to a temperature above the body lumen temperature, e.g., 45 degrees C, before insertion. After insertion, the body lumen brings the coil's temperature down to about 37 degrees C. In any of this embodiments, temperature, current, and the like are used to cause the tight coil to become activated, deployed, positioned, and seated in the respective body lumens. This enables the coil to take its deployed shape. In all of these embodiments, the reverse temperature parameter is applied to the coil when it is removed. This causes a collapse of the coil.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope and this invention.

What is claimed is:

1. An anastomosis device, comprising:
   a catheter having a catheter distal end to be placed in a patient's body and a catheter proximal end, the catheter having a tube with a main lumen extending from substantially the catheter proximal end to substantially the catheter distal end of the, the tube including a first cut-out portion and a first distensible member positioned adjacent to the first cut-out portion, the catheter including an actuating device to distend and un-distend the distensible member; and
   a passive fixation device positioned around the tube of the catheter comprising, a generally elongated body with a proximal end and a distal end, with a non-deployed distal end and a non-deployed proximal end in a non-deployed position, and the proximal end being expanded to a deployed proximal end in a deployed position by distending the first distending member, the distal end being expanded to a deployed distal end in a deployed position by distending the first distending member, each of the ends being in the non-deployed positions while being inserted into a body lumen, and each end becoming expanded in the deployed position after insertion in the body lumen, wherein the distal end is inserted into a first body lumen, and the proximal end is inserted into a second body lumen.

2. The anastomosis device of claim 1, wherein the catheter includes a second cut-out portion in the tube, and a second distensible member positioned adjacent the second cut-out portion.

3. The anastomosis device of claim 1, wherein the first and second members are first and second balloons respectively, and the actuating member is an inflation and deflation device for inflating and deflating the balloons.

4. The anastomosis device of claim 3, wherein the passive fixation device comprises a coiled passive fixation device distal end and a coiled passive fixation device proximal end connected by a connecting member.

5. The anastomosis device of claim 3, wherein the first and second balloons are inflated and expanded at different times by the inflation and deflation device.

6. The anastomosis device of claim 3, wherein the first balloon is configured to inflate to a substantially cylindrical configuration, and the second balloon is configured to inflate to a substantially conical configuration.

7. The anastomosis device of claim 1, wherein the first body lumen is a bladder and the second body lumen is an urethra.

8. A method for the anastomosis of a bladder to a urethra, comprising:
   providing an anastomosis device including, a catheter with a tube including a main lumen and at least one inflatable balloon, the catheter including a distal end and a proximal end, and a passive fixation device positioned at the exterior of the catheter around the tube, the passive fixation device including a passive fixation device distal end and a passive fixation device proximal end with each being expandable to deployed positions and each end of the passive fixation device being non-expanded in non-deployed positions;
   introducing the anastomosis device into the urethra with the proximal and distal ends of the passive fixation device being in non-deployed positions;
   deploying the passive fixation device proximal end in the urethra to the deployed position so the passive fixation device proximal end becomes retained in the urethra; and
   deploying the passive fixation device distal end in the bladder to a deployed position so the passive fixation device distal end becomes retained in the bladder.

9. The method of claim 8, further comprising moving the urethra to a position adjacent to a bladder after the passive fixation device proximal end has been deployed and becomes retained in the urethra.

10. The method of claim 8, further comprising removing the catheter from the urethra after the passive fixation device proximal and distal ends have been deployed and retained in the urethra and bladder.

11. The method of claim 8, further comprising removing the passive fixation device from the bladder and urethra after anastomosis of the bladder and urethra is completed.

* * * * *